(12) United States Patent
Bomsel et al.

(10) Patent No.: US 8,883,742 B2
(45) Date of Patent: Nov. 11, 2014

(54) PEPTIDE INCREASING FUSIOGENIC CAPACITY OF A GAMETE

(75) Inventors: Morgane Bomsel, Paris (FR); Jean-Philippe Wolf, Paris (FR)

(73) Assignees: Universite Paris 13, Villetaneuse (FR); Centre National de la Recherche Scientifique, Paris Cedex (FR)

( * ) Notice: Subject to any disclaimer, the term of this patent is extended or adjusted under 35 U.S.C. 154(b) by 1977 days.

(21) Appl. No.: 10/579,921

(22) PCT Filed: Nov. 19, 2004

(86) PCT No.: PCT/FR2004/002956
§ 371 (c)(1),
(2), (4) Date: May 19, 2006

(87) PCT Pub. No.: WO2005/051799
PCT Pub. Date: Jun. 9, 2005

(65) Prior Publication Data
US 2007/0082839 A1     Apr. 12, 2007

(30) Foreign Application Priority Data
Nov. 19, 2003 (FR) ..................... 03 13545

(51) Int. Cl.
| | | |
|---|---|---|
| *A61K 38/08* | (2006.01) | |
| *C07K 5/12* | (2006.01) | |
| *C07K 14/705* | (2006.01) | |
| *C07K 7/06* | (2006.01) | |
| *C07K 7/64* | (2006.01) | |
| *A61K 38/00* | (2006.01) | |

(52) U.S. Cl.
CPC . *C07K 7/06* (2013.01); *C07K 5/123* (2013.01); *C07K 14/705* (2013.01); *C07K 7/64* (2013.01); *A61K 38/00* (2013.01); *C07K 5/126* (2013.01)
USPC ........................................................ 514/21.8

(58) Field of Classification Search
None
See application file for complete search history.

(56) References Cited

U.S. PATENT DOCUMENTS
5,849,865 A     12/1998  Ingram et al.

FOREIGN PATENT DOCUMENTS
WO     96/00581     1/1996

OTHER PUBLICATIONS

Krstenansky et al (Biochimica et biophysica acta 957 (1988) 53-59).*
Li et al 'Screening an alpha-glucosidase inhibitor from a phage-displayed peptide library' Acta Biochimica et Biophysica Sinica v33(5) 2001 pp. 513-518.*
Translation of Li et al 'Screening an alpha-glucosidase inhibitor from a phage-displayed peptide library' Acta Biochimica et Biophysica Sinica v33(5) 2001 pp. 513-518; the translation document is 17 pages along with a cover page.*
International Search Report of PCT/FR2004/002956, mailed Jan. 31, 2006.
Evans et al, "Mouse sperm-egg plasma membrane interactions: Analysis of roles of egg integrins and the mouse sperm homologue of PH-30 (fertilin) beta", Journal of Cell Science, vol. 108, No. 10, 1995, pp. 3267-3278, XP002289784.
Myles et al., "Identification of a binding site in the disintegrin domain of fertilin required for sperm-egg fusion", Proceedings of the National Academy of Sciences of the United States of America, vol. 91, No. 10, 1994, pp. 4195-4198, XP002289785.
Gupta et al., "Characterization of fertilin beta-disintegrin binding specificity in sperm-egg adhesion", Bioorganic & Medicinal Chemistry, Apr. 2000, vol. 8, No. 4, pp. 723-729, XP002289786.
Bronson et al., "Evidence that a functional fertilin-like ADAM plays a role in human sperm-oolemmal interactions", Molecular Human Reproduction, May 1999, pp. 433-440, XP002289787.

* cited by examiner

*Primary Examiner* — James H Alstrum Acevedo
*Assistant Examiner* — Ronald Niebauer
(74) *Attorney, Agent, or Firm* — Nixon & Vanderhye P.C.

(57) ABSTRACT

The invention relates to a cyclic peptide increasing the fusiogenic capacity of the oocyte arising from the disintegrin loop of fertilin beta, to a pharmaceutical composition comprising said cyclic peptide and to the use thereof, particularly in order to supplement culture media used to carry out in vitro fertilization.

6 Claims, 6 Drawing Sheets

PEPTIDE INCREASING FUSIOGENIC CAPACITY OF A GAMETE

This application is the US national phase of international application PCT/FR2004/002956, filed 19 Nov. 2004, which designated the U.S. and claims priority of FR 0313545, filed 19 Nov. 2003, the entire contents of each of which are hereby incorporated by reference.

TECHNICAL FIELD

The invention relates to cyclic peptides increasing the fusiogenic capacity of the oocyte and/or the spermatozoon, to pharmaceutical compositions comprising the same and to the uses thereof, particularly in order to supplement culture media used to carry out in vitro fertilization. The inventive peptides typically comprise a domain arising from the disintegrin loop of fertilin beta.

STATE OF THE ART

Fertilization is a complex process leading to the fusion of gametes (spermatozoon and oocyte) to form an embryo. This natural process takes place in the tubalar ampulla and results in pregnancy after migration of the embryo to the uterine cavity.

When a couple is infertile, Medically Assisted Reproduction techniques are used to obtain embryos in vitro. The embryos are then transferred through the vagina into the uterus where they become implanted.

In vitro fertilization simply consists of contacting oocytes and spermatozoa, in a suitable culture medium and in suitable conditions of pH and temperature, so that fertilization can take place. Methods have been widely developed over the past 25 years (Bavister 2002).

When, for reasons that are not always clear, fertilization fails, biologists can resort to assisted fertilization techniques whereby a sperm cell is injected directly into the oocyte cytoplasm. However, the development of microinjected embryos is not as good as that observed after spontaneous fertilization. In fact, the pregnancy rate after transfer of such embryos is lower than after simple in vitro fertilization (25.4% vs 26.5%, on over 20,000 attempts) (FIVNAT, 2001). Likewise, embryos produced by microinjection are less tolerant to freezing than those obtained by IVF (BLEFCO 2001; Simon et al., 1998). For instance, embryo lysis is more likely during thawing and a lower implantation rate is obtained.

Lastly, it is known that activation of the oocyte following fertilization is mediated by calcium oscillations induced by a sperm-derived factor (Swann 1999). These oscillations have a regulated amplitude and frequency on which the quality of the embryo depends (Swann 1999). Short-circuiting the membrane steps of the gamete interaction modifies the nature of these calcium waves for two reasons. The physiological interaction between the membranes does not take place, and the trauma to the cell from introducing the microinjection pipette into the cytoplasm causes calcium outflow from the reservoirs (Tésarik et al. 2002). While this outflow ensures oocyte activation, it can also perturb the subsequent development of the embryo.

The study of the process of fusion between the sperm and egg membranes at fertilization has partially revealed the mechanism of membrane fusion.

Formation of a membrane molecular complex takes place at the oocyte surface. Said complex is induced by the spermatozoon at fertilization. Its composition and mechanism of action have not been fully elucidated, but it is known that inhibition of its formation leads to inhibition of gamete fusion. Fertilization is therefore clearly related to the formation of these patches at the oocyte surface.

The commonly accepted hypothesis is that the spermatozoon interacts with the membrane through a first receptor and that after transduction of a transmembrane signal, a cellular mechanism enables formation of these patches to which the spermatozoon attaches.

Research has been undertaken to determine the nature of the sperm ligand and the oocyte receptor involved. There is a protein in the spermatozoon membrane called fertilin (Evans 2002). This molecule is an alpha beta dimer the molecules of which belong to the ADAM protein family (A Disintegrin And Metalloprotease) (Evans 2001). The presence of integrins has been demonstrated on the oocyte. Sperm fertilin, through its putative binding site, can interact with one or more oocyte integrins.

Membrane molecules called integrins are binding molecules which play a role in cell-extracellular matrix and cell-cell binding. Their ligands bind to their extracellular domain via a binding site composed of a tripeptide located at the tip of a loop.

Spermatozoa contain a membrane molecule with a disintegrin site that can bind integrin. This molecule, discovered in the guinea pig but present in all mammals studied so far including humans and mice, is called fertilin. Human fertilin has been sequenced and so its putative binding site is known, which is the FEE tripeptide (phenylalanine, glutamic acid, glutamic acid) (Gupta et al. 1995; Vidaeus et al.; 1997). A linear octapeptide containing the FEE sequence inhibits the adhesion and penetration of sperm to the oocyte (Bronson 1999). Similar inhibitory effects have been observed in other species with linear and cyclic peptides (Mwethera 1999; Gupta 2000; Li 2002; Myles 1994). Evans (1995) reported an absence of inhibitory effect of cyclic peptides in mice.

DESCRIPTION OF THE INVENTION

During their research on inhibitors of fertilization, the inventors synthesized a cyclic peptide called FEEc containing the binding site of human fertilin beta and tested the effect thereof on human oocytes. In a surprising and unexpected manner, the inventors thereby showed that (1) the cyclic peptide FEEc binds the human oocyte membrane, (2) it induces displacement of adhesion proteins to the oocyte surface, said displacement normally being induced by spermatozoa, (3) it increases the fusiogenic capacity of oocytes. These findings were corroborated by experiments in mice.

Thus, the inventors have identified a novel class of cyclic peptides capable of increasing the fusiogenic capacity of oocytes and/or spermatozoa. In addition, said class of cyclic peptides would presumably be capable of activating oocytes.

The invention relates to the use of a cyclic peptide comprising the binding site of fertilin beta (ADAM 2) to oocyte integrin in order in order to increase the fusiogenic capacity and/or to active an oocyte, typically in vitro or ex vivo. Said binding site is contained in the disintegrin loop of fertilin beta. Said cyclic peptide minimally comprises the tripeptide essential for this binding. This tripeptide differs according to species. However, the organization of the disintegrin loop is very highly conserved between species (Table 1). It will therefore be easy for those skilled in the art to define the disintegrin loop of fertilin beta and identify the tripeptide.

TABLE 1

| | | Disintegrin loop | |
|---|---|---|---|
| Human | (436)CLFMSKERMC | RPSFEECDLP EYCNGSSASC(465) | SEQ ID No 1 |
| Mouse | (440)CKLKRKGEVC | RLAQDECDVT EYCNGTSEVC(469) | SEQ ID No 2 |
| Guinea pig | (433)CEFKTKGEVC | RESTDECDLP EYCNGSSGAC(462) | SEQ ID No 3 |
| Rabbit | (435)CTFKERGQSC | RPPVGECDLF EYCNGTSALC(464) | SEQ ID No 4 |
| Macaque | (436)CLFMSQERCC | RPSFDECDLP EYCNGTSASC(465) | SEQ ID No 5 |
| Bovine | (435)CAFIPKGHIC | RGSTDECDLH EYCNGSSAAC(464) | SEQ ID No 6 |
| Rat | (441)CNLKAKGELC | RPANQECDVT EYCNGTSEVC(470) | SEQ ID No 7 |
| Pig | (435)CSFMAKGQTC | RLTLDECDLL EYCNGSSAAC(464) | SEQ ID No 8 |

The positions shown in parentheses correspond to the positions in the fertilin beta sequences referenced hereinafter. Residues underlined in bold type correspond to the tripeptide. Residues in bold type are perfectly conserved between species A consensus sequence for the disintegrin loop can be deduced from Table 1.

(SEQ ID NO: 12)
$C-X_2-(F/L)-(K/M/I)-X_5-(K/R/Q)-(G/E)-X_8-X_9-C-R-X_{12}-X_{13}$-TriPept-$C-D-(L/V)-X_{20}-E-Y-C-N-(G/E)-(T/S)-S-(A/E/G)-X_{29}-C$ wherein the X groups represent, independently of one another, an amino acid and "TriPept" is the tripeptide essential for binding of fertilin to integrin. Preferably, $X_8$ is a charged amino acid. More particularly, it is selected in the group consisting of E, R and Q. Preferably, $X_{12}$ is selected in the group consisting of P, L, E, and G. Preferably, $X_{13}$ is a small and uncharged amino acid, more particularly selected in the group consisting of S, A, P, and T. Preferably, $X_{29}$ is a small and uncharged amino acid, more particularly selected in the group consisting of S, A, and V.

The cyclic peptide can be cyclized by any method known to those skilled in the art. The peptide can be cyclized by means of a covalent bond between the main chain and the main chain, between the main chain and a side chain, or between a side chain and another side chain. Said bond can be a disulfide, amide or thioether bond.

For example, the peptide can be cyclized by a peptide bond between the N-terminal residue and the C-terminal residue, or with amino or carboxylic groups of the side chains of the residues.

Preferably, the peptide is cyclized by means of two cysteine residues, more particularly by means of a disulfide bridge between said two cysteine residues. The cysteine residues must be located in such as way as to permit cyclization of the peptide. The cysteine residues can be located in such a way that, after cyclization, the peptide has a polypeptide tail. Preferably, said cysteine residues are located at the ends of the peptide.

The cyclic peptide according to the invention can therefore be described by the following formula:

wherein X represents an amino acid, m and n are comprised between 0 and 14. As indicated earlier, in the inventive formulas, the X groups are independent of one another and can represent, within a same molecule, amino acids which are the same or different. Preferably, when m or n is equal to 0, the other is at least 1. Preferably, m+n is less than 10, preferably less than or equal to 5. In a preferred embodiment, m+n is equal to 3. Preferably, the tripeptide contains a sequence X-(Q/D/E)-E, preferably X-(D/E)-E. For example, the tripeptide can be selected in the group consisting of (Q-D-E), (F-E-E), (T-D-E), (V-G-E), (F-D-E), (T-D-E), (N-Q-E), (L-D-E). In a preferred embodiment, the tripeptide is (F-E-E).

In a preferred manner, the cyclic peptide according to the invention is described by the following formula:

The cysteine residues involved in peptide cyclization can be naturally located in the disintegrin loop or can be introduced into the peptide sequence. The disintegrin loops are rich in cysteine. In fact, cysteine residues are conserved at positions positions 1, 10, 17, 23 and 30 of said loops. Thus, the peptides can be cyclized by means of a disulfide bridge selected in the group consisting of: C1-C17, C1-C23, C1-C30, C10-C17, C10-C23, and C10-C30. Preferably, the peptides are cyclized by means of a disulfide bridge selected from C10-C17 and C10-C23.

The cyclic peptides according to the invention can therefore display one of the following structures:

(SEQ ID NO: 10)
$C_1-X2-(F/L)-(K/M/I)-X_5-(K/R/Q)-(G/E)-X_8-X_9-C-R-X_{12}-X_{13}$-TriPept-$C_{17}$;

(SEQ ID NO: 11)
$C_1-X2-(F/L)-(K/M/I)-X_5-(K/R/Q)-(G/E)-X_8-X_9-C-R-X_{12}-X_{13}$-TriPept-$C-D-(L/V)-X_{20}-E-Y-C_{23}$;

(SEQ ID NO: 12)
$C_1-X2-(F/L)-(K/M/I)-X_5-(K/R/Q)-(G/E)-X_8-X_9-C-R-X_{12}-X_{13}$-TriPept-$C-D-(L/V)-X_{20}-E-Y-C-N-(G/E)-(T/S)-S-(A/E/G)-X_{29}-C_{30}$;

(SEQ ID NO: 13)
$C_{10}-R-X_{12}-X_{13}$-TriPept-$C_{17}$;

(SEQ ID NO: 14)
$C_{10}-R-X_{12}-X_{13}$-TriPept-$C-D-(L/V)-X_{20}-E-Y-C_{23}$;

(SEQ ID NO: 15)
$C_{10}-R-X_{12}-X_{13}$-TriPept-$C-D-(L/V)-X_{20}-E-Y-C-N-(G/E)-(T/S)-S-(A/E/G)-X_{29}-C_{30}$;

wherein X represents an amino acid and the cysteine residues at the ends of the peptide form disulfide bridges.

Preferably, the cyclic peptides according to the invention display one of the following structures:

$C_{10}$-R-$X_{12}$-$X_{13}$-TriPept-$C_{17}$; (SEQ ID NO: 13)
or $C_{10}$-R-$X_{12}$-$X_{13}$-TriPept-C-D-(L/V)-$X_{20}$-E-Y-$C_{23}$. (SEQ ID NO: 14)

More particularly, the cyclic peptides according to the invention are selected in the group consisting of the fragments 1-17, 1-23, 1-30, 10-17, 10-23, and 10-30 of one of the sequences SEQ ID Nos 1-8, preferably of sequence SEQ ID No 1. Preferably, the cyclic peptides according to the invention are selected in a group consisting of fragments 10-17, 10-23 of one of the sequences SEQ ID Nos 1-8, preferably of sequence SEQ ID No 1.

The cysteine residues can be introduced into the peptide to be cyclized. In a preferred embodiment, the inventive peptide has the following structure:

(SEQ ID NO: 16)

wherein X is an amino acid. A small and uncharged amino acid will be preferred. Preferably, X is selected in the group consisting of A, S or T. More particularly, X is A or S. In a preferred embodiment, X is serine and the tripeptide has the sequence (F-E-E) (SEQ ID No 9). More particularly, the invention relates to said cyclic peptide (named FEEc in the examples) and to the use thereof for increasing the fusiogenic capacity of and/or for activating oocytes.

The amino acids of the cyclic peptide according to the invention can be natural or not. A non-natural amino acid denotes an analogue or derivative of a natural amino acid. For example, a non-natural amino acid can have a longer, shorter or different side chain containing suitable functional groups. It is understood that consideration is taken of L and D stereoisomers. In addition, the peptide bonds can be modified to make them resistant to proteolysis. For example, at least one (—CO—NH—) peptide bond can be replaced by a divalent bond selected in the group consisting of ($—CH_2—NH—$), (—NH—CO—), ($—CH_2—O—$), ($—CH_2—S—$), ($—CH_2—CH_2—$), ($—CO—CH_2—$), ($—CHOH—CH_2—$), (—N═N—), and (—CH═CH—).

The residues of the sequences described hereinabove can vary in a conservative manner. Conservative is understood to mean that the variant residue displays similar physico-chemical characteristics. Steric hindrance, polarity, hydrophobicity or charge are among the physico-chemical characteristics taken into account.

Consequently, the invention also relates to variants and/or derivatives of said cyclic peptides and to the use thereof, particularly in order to increase the fusiogenic capacity and/or to activate oocytes. Said variants and derivatives conserve the binding capacity to oocyte integrin, more particularly of integrin α6β1.

The invention also relates to a multimer of the inventive cyclic peptide. This polymerization of the cyclic peptide can be achieved by any method known to those skilled in the art. Preferably, the cyclic peptide is coupled with a carrier molecule allowing the peptide to polymerize. The bond between the cyclic peptide and the carrier molecule can be covalent or noncovalent. The methods by which to attach the cyclic peptide to the carrier molecule are well known to those skilled in the art and comprise amine chemistry, carbodiimide coupling of carboxyl and amino derivatives, activation of cyanogen bromide, N-hydroxysuccinimide, epoxide, sulfhydryl, or hydrazide. The bond between the carrier molecule and the cyclic peptides can be direct or indirect. When it is indirect, it can take place through a linker. Said linker can play a role of spacer which avoids interference of the carrier molecule on the properties of the cyclic peptide, particularly the fusiogenic and/or activator properties. Said linker can be a peptide. The cyclic peptide must be attached to the carrier molecule in such a way as to maintain the accessibility of the tripeptide. The number of cyclic peptides comprised in the multimer is preferably comprised between 2 and 1000. The multimeric form of the inventive peptide makes it possible to increase the effect of the cyclic peptide on the displacement of oocyte adhesion proteins.

For example, the polymerization can be accomplished by means of a biotin/streptavidin conjugate which allows a tetramer of the cyclic peptide to be prepared, whereby each cyclic peptide is bound to a biotin and four biotins can bind to a streptavidin molecule.

Alternatively, several cyclic peptides according to the invention can be carried on a transport protein. Preferably, said protein does not have any biological effect on the oocyte. Those skilled in the art know of several proteins used as carrier proteins including bovine serum albumin (BSA) and limpet hemocyanin.

Moreover, several cyclic peptides according to the invention can be immobilized on a solid support. Non-limiting examples of the solid support are agarose, glass, cellulose resins, silica resins, polystyrene, and polyacrylamide. The solid support can be modified with functional groups allowing fixation of the cyclic peptides, for example by means of carboxyl, amino, sulfhydryl, hydroxyl and/or carbohydrate groups contained in said peptides.

The invention concerns a composition comprising a cyclic peptide according to the invention or a multimer of the same. Said composition can be a medium intended for culturing gametes. Said composition can also comprise a pharmaceutically acceptable support. Said composition can be a pharmaceutical composition, preferably suitable for local application. Preferably, said local application takes place in the female genital tract.

The invention concerns the use of a cyclic peptide according to the invention, a multimer of the same or a composition according to the invention in order to increase the fusiogenic capacity of a gamete, in particular the oocyte, or to activate an oocyte, and a corresponding method.

In particular, the cyclic peptides according to the invention can be used for in vitro fertilization, for artificial insemination and for nuclear transfer (cloning) in mammals, preferably non-human. Preferably, said peptides will be used to carry out or to improve in vitro fertilization, more particularly in humans. In this respect, the invention also concerns a gamete culture medium supplemented with a cyclic peptide according to the invention or a multimer of the same. In a particular embodiment, the oocyte is contacting with the cyclic peptide according to the invention before being incubated with sperm. In another embodiment, the oocyte is contacting simultaneously with the cyclic peptide according to the invention and the male gamete.

The inventive peptides can also be used in a treatment designed to enhance fertility. Thus the invention concerns the use of an inventive peptide for preparing a medicament intended for the treatment of fertility problems, and a corresponding method.

The cyclic peptides according to the invention can also be used to potentiate spermatozoa.

The different methods and uses of the invention can be carried out in vitro, ex vivo or in vivo. Advantageously, they are carried out in vitro or ex vivo so as to produce treated biological materials or cells.

The cyclic peptides according to the invention can be used for any species the reproduction of which involves gametes. The invention is of particular interest for endangered species, species with low fertility or highly valuable species. More particularly, the invention contemplates the use of the cyclic peptides in mammals. Preferably, the invention can be used in the reproduction or cloning of ovines, bovines, equines, etc. It is understood that the invention can also be used to assist human procreation.

Said peptide added to culture media for human gametes can potentiate the fusiogenic capacity of the latter and lead to the formation of embryos all while not interfering with physiological membrane interactions. The use of said peptide has two potential interests: reducing the use of intracytoplasmic microinjection as a fertilization technique and improving the quality of the embryos obtained.

The invention further concerns methods for screening compounds increasing the fusiogenic capacities of the oocyte. Said method comprises the following steps: 1) incubating the oocyte in the presence of the test compound; and 2) evaluating the ability of the compound to increase the fusiogenic capacity of the oocyte. In a preferred manner, fusiogenic capacity can be estimated by at least one of the following criteria: binding to the oocyte, induction of adhesion protein displacement to the oocyte surface (more particularly of integrin α6β1), fusion of the oocyte with a spermatozoon. Preferably, displacement of adhesion proteins to the oocyte surface leads to the formation of patches of adhesion proteins (more particularly of integrin α6β1). The displacement of adhesion proteins can be evaluated by the labelling of the same.

The invention relates to compounds inducing the redistribution of oocyte adhesion proteins into patches and to the use thereof for increasing the fusiogenic capacities of oocytes.

Other aspects and advantages of the invention will become apparent in the following examples, which are given for purposes of illustration and not by way of limitation.

EXAMPLES

Results of the Study of Cyclic Peptide FEEc on Human Gamete Fusion

Materials and Methods
Human Oocytes

The human oocytes used in the experiments were from two sources: oocytes which failed to be fertilized after IVF and oocytes which were not microinjected due to immaturity at the time of ICSI and matured in vitro. Patients donated said oocytes for research purposes and signed a consent form approved by the Institutional Review Board of the Aulnay-sous-Bois hospital.

These oocytes aged 48 hours or matured in vitro were not or were no longer capable of producing an embryo. Moreover, the polyspermy blocking mechanism which ensures that the embryo will be diploid is located in the zona pellucida of the oocyte. By removing the zona pellucida of these oocytes, this protective mechanism is abolished, leading to nonviable polyspermic zygotes in the event of gamete fusion. Finally, as embryo development occurs inside the zona pellucida for the first six days, the absence of the latter precludes said development from taking place.

To maintain the oocyte membrane as close as possible to its natural state, the inventors removed the zona pellucida mechanically with microsurgical scissors.
Spermatozoa Sperm from fertile donors was collected after three days of abstinence and prepared as for IVF. Briefly, the ejaculate was placed at 37° C. until liquefication and then selected on a 2 layer Puresperm gradient (90 and 45%). The sperm was then kept in capacitating conditions until insemination of the oocytes.
Synthetic Cyclic Peptide FEEc The complete sequence of the disintegrin domain of human fertilin constituting the loop is shown below:

CLFMSKERMCRPSFEECDLPEYCNGSSASC    SEQ ID No 1

The synthetic cyclic peptide FEEc used in this example is as follows:

CSFEEC    SEQ ID No 9

The FEEc peptide synthesized by the inventors comprises the sequence of the FEE tripeptide. It comprises the Serine preceding said sequence and the Cysteine following it. The inventors introduced another Cysteine upstream of the binding site. The two cysteines located at the ends of the peptide enabled the cyclization thereof.
Immunofluorescence The integrin alpha 6 subunit is present on the human oocyte membrane. It forms part of the multimolecular fusion complex. It is for this reason that the inventors used it as a control of membrane reorganization.

Zona-free oocytes were incubated in 20 µl drops of Ferticult culture medium under oil at room temperature. The medium was supplemented with 20 µM mouse anti-human alpha 6 antibody (Chemicon International, London, GB). The oocytes were then washed and fixed in 2% PFA for 1 hour. They were then incubated for 45 minutes with a second donkey anti-mouse immunoglobulin antibody labelled with FITC or rhodamine (FITC-conjugated donkey anti-mouse IgG or Rhodamine-conjugated donkey anti-mouse IgG 10 µg/ml; Jackson Laboratories). The oocytes were washed and mounted in antifade Immunomount (Shandon Laboratories) between the coverslip and slide and examined either under a fluorescence microscope (Zeiss Axiophot) or a confocal microscope (Leica Lasertechnik, GmbH).
Functional Fusion Assays Functional tests of inhibition of fusion were carried out in conditions similar to those used for IVF, that is, in conditions sufficiently close to physiological conditions since they enable pregnancy and fetuses. Briefly, the oocytes were incubated in 20 µl drops of Ferticult under oil for 18 hours in a 5% $CO_2$ incubator at 37° C. with 4000 mobile sperm cells. The tests were carried out by supplementing the medium with the FEEc peptide at 200 µM concentration. At the end of incubation, the oocytes were washed and incubated for 20 minutes in Hoechst 33342 (Sigma) 5 µg/ml. After fixation in 4% PFA 1% PBS-BSA for 30 minutes at room temperature, the oocytes were mounted in Immunomount between the coverslip and the slide and examined under ultraviolet light. Fused spermatozoa were fluorescent. The slides were analyzed under a Zeiss Axiophot microscope equipped with a camera connected to Imaging System Package image analysis software (Applied Imaging, Newcastle-upon-Tyne, UK).

Results
Immunofluorescence and Confocal Microscopy.

Figure 1A:
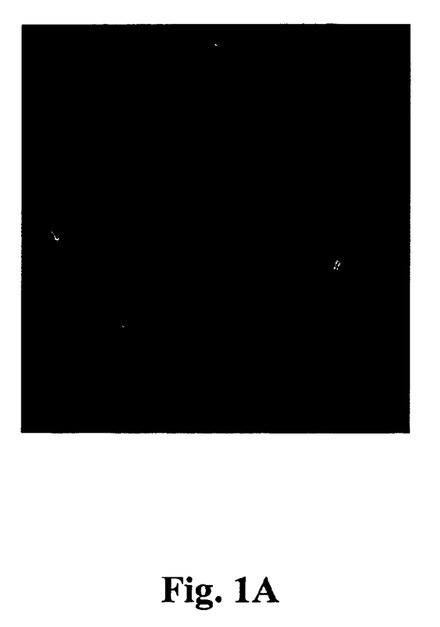
FIG. 1. Detection of biotinylated FEEc peptide at the surface of human oocytes.
Figure 1B:
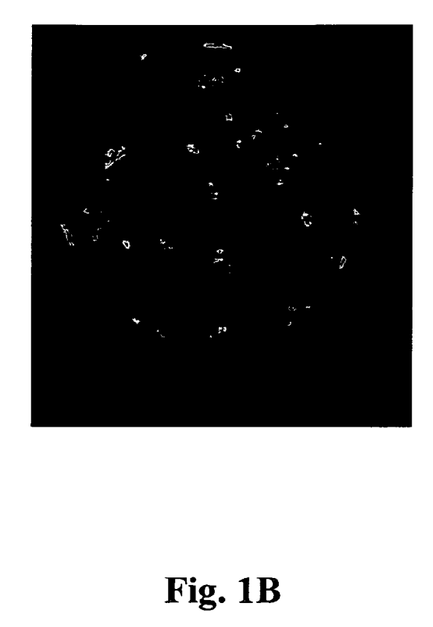

The oocytes were incubated with 200 µM biotinylated FEEc peptide for 45 minutes. Confocal microscopy was used to reveal labelling of the membrane with the FEEc peptide as seen on the oocyte equatorial segment (FIG. 1A). Computerized superimposition showed that this labelling corresponded to membrane patches (FIG. 1B).

Induction of Fusion Patches by the FEEc Peptide on Human Oocytes

Figure 2A:
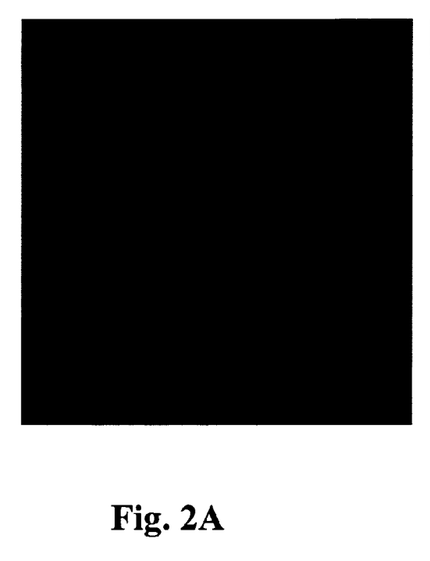
FIG. 2. Induction of fusion patches on human oocytes by FEEc peptide.
Figure 2B:
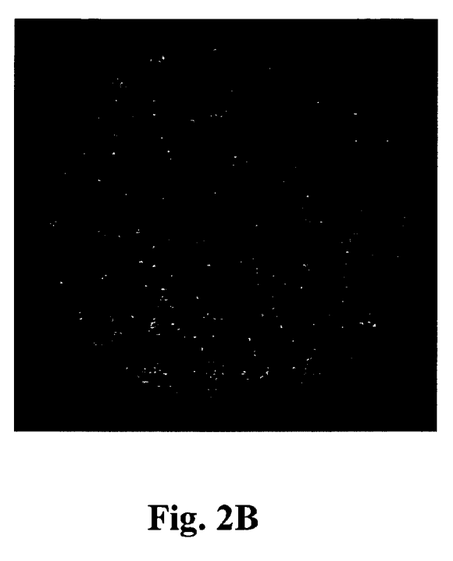

The spermatozoa induced the formation of multimolecular patches. By incubating oocytes matured in vitro with a suspension of 200 µM of FEEc peptide for 18 hours, the inventors demonstrated a redistribution of the integrin α6 subunit. In fact, while the distribution of the α6 subunit on the surface of intact oocytes was homogeneous (FIG. 2A), the FEEc peptide induced the redistribution thereof in the form of small membrane patches. In mice, spermatozoa induce said patches during fertilization. It can be concluded that the FEEc peptide induces a redistribution of adhesion proteins on the membrane similar to that induced by the sperm cell itself at fertilization.

Functional Fusion Assay with Human Gametes

Figure 3A:
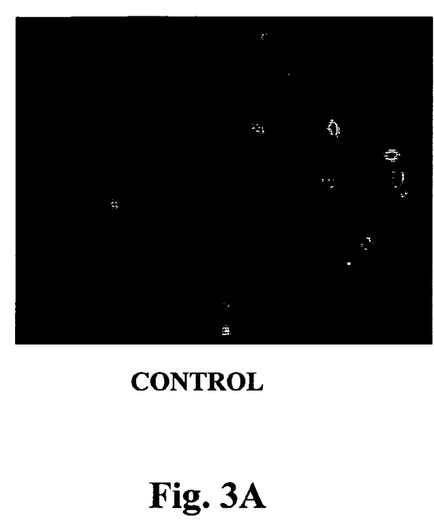
FIG. 3. Functional fusion assay with human gametes.
Figure 3B:
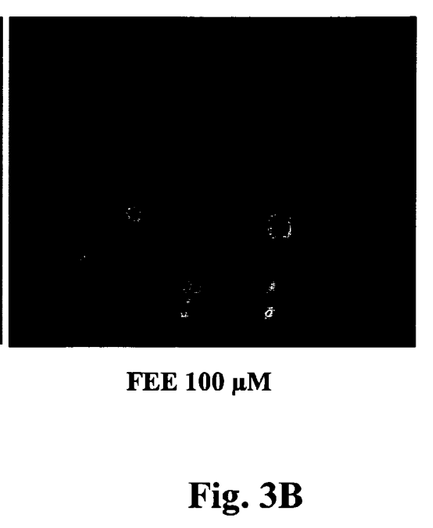
Figure 4:
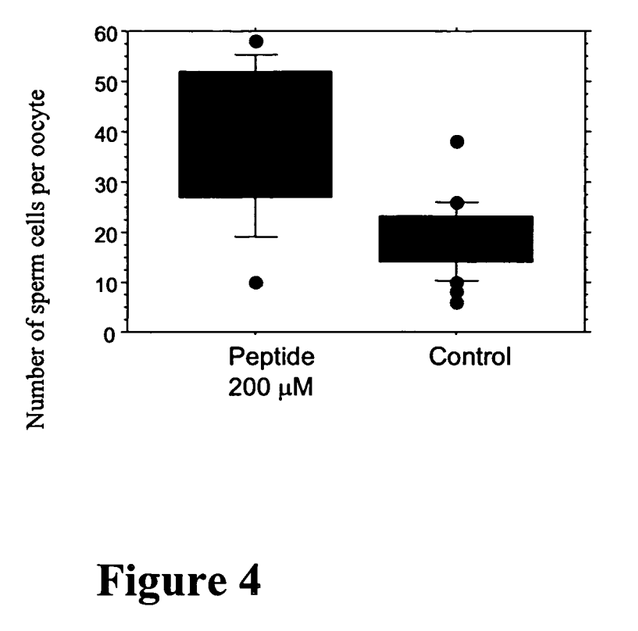
FIG. 4. Effects of the FEEc peptide on fertilization of human oocytes.

In similar conditions, zona-free oocytes were incubated with 200 µM FEEc peptide and spermatozoa. In the control oocytes, about twenty fused sperm cells could be seen in the oocyte cytoplasm (FIG. 3A). In the presence of 200 µM FEEc peptide, the number of spermatozoa in the cytoplasm was much higher (FIG. 3B). The experiment was conducted on a larger number of oocytes and revealed a mean 60% increase in the number of spermatozoa that fused with the oocyte (26.1±8.3 vs 16.4±5.2; P<0.001). The increase in the number of spermatozoa was therefore statistically significant. This effect was specific because incubation with the same scrambled peptide had no effect. The action of the FEEc peptide was reversible because oocytes preincubated with the FEEc peptide then washed and inseminated showed no change in their fusiogenic capacity. Thus there is no toxic effect on oocytes, although co-incubation is necessary for the effect of the peptide to appear.

Discussion

The FEEc peptide therefore has the property of increasing the fusiogenic capacity of human oocytes. It mimics the mechanism by which the spermatozoon induces molecular fusion complexes on the oocyte upon contact with the oocyte membrane and therefore facilitates the fusion process.

It can be used to supplement the culture media used to carry out in vitro fertilization, in which case it should improve the fertilization rate of IVF carried out for idiopathic infertility or sperm deficiency. This would lower the need for microinjection techniques and improve embryo quality.

Results of the Study of Cyclic QDE on Gamete Fusion in Mice

In line with what was observed in humans, the effect of a cyclic tripeptide was studied in the mouse model. By analogy, the tripeptide motif in this case contained the disintegrin binding site of mouse fertilin β, that is, the QDE tripeptide. This peptide was named QDEc.

Materials and Methods.

Six-week-old C56bl/CBA mice were hyperstimulated with 5 IU PMSG and 5 IU hCG administered at a 48 hour interval. Thirteen hours after the last injection, the mice were sacrificed and the oviducts removed and lacerated in M2 medium. The oocytes were retrieved and either inseminated in their cumulus or decoronized by a short treatment with hyaluronidase. Decoronized oocytes were then mechanically stripped of their zona pellucida with microdissection scissors under a binocular magnifier.

Zona-free oocytes were preincubated for 30 minutes and then inseminated in the presence of (1) M16 medium for the control group; (2) medium supplemented with 10 µM QDEc; (3) 100 µM QDEc and (4) 1 mM QDEc. In all cases the oocytes were inseminated for 3 hours with $10^6$ mobile sperm per ml.

Intact ovocytes were incubated with 100 µM QDEc and $10^5$ sperm/ml.

After incubation, the oocytes were thoroughly washed and incubated in 10 µM Hoescht for 30 minutes, rinsed and then examined in ultraviolight light under a Zeiss microscope. The data were analyzed with Statview® software.

Results
1—Zona-Free Oocytes

Figure 5:
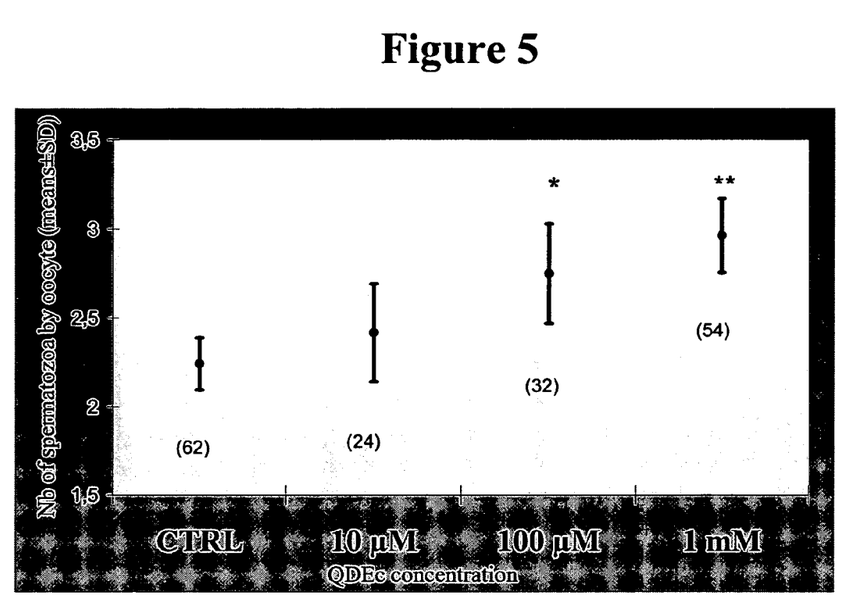
FIG. 5. Effects of the FEEc peptide on gamete fusion in mice.

In five experiments, 170 oocytes were studied in four groups. While the mean number of fused sperm per oocyte was 2.2±0.1 (mean±SD) in the control group, it increased in a dose-dependent manner when QDE was present in the incubation medium (FIG. 5), showing a statistical difference at 100 µM concentration (P<0.05) and statistical significance at 1 mM (p<0.004), with a 32% increase in the number of fused spermatozoa.

2—Intact Oocytes

Figure 6:
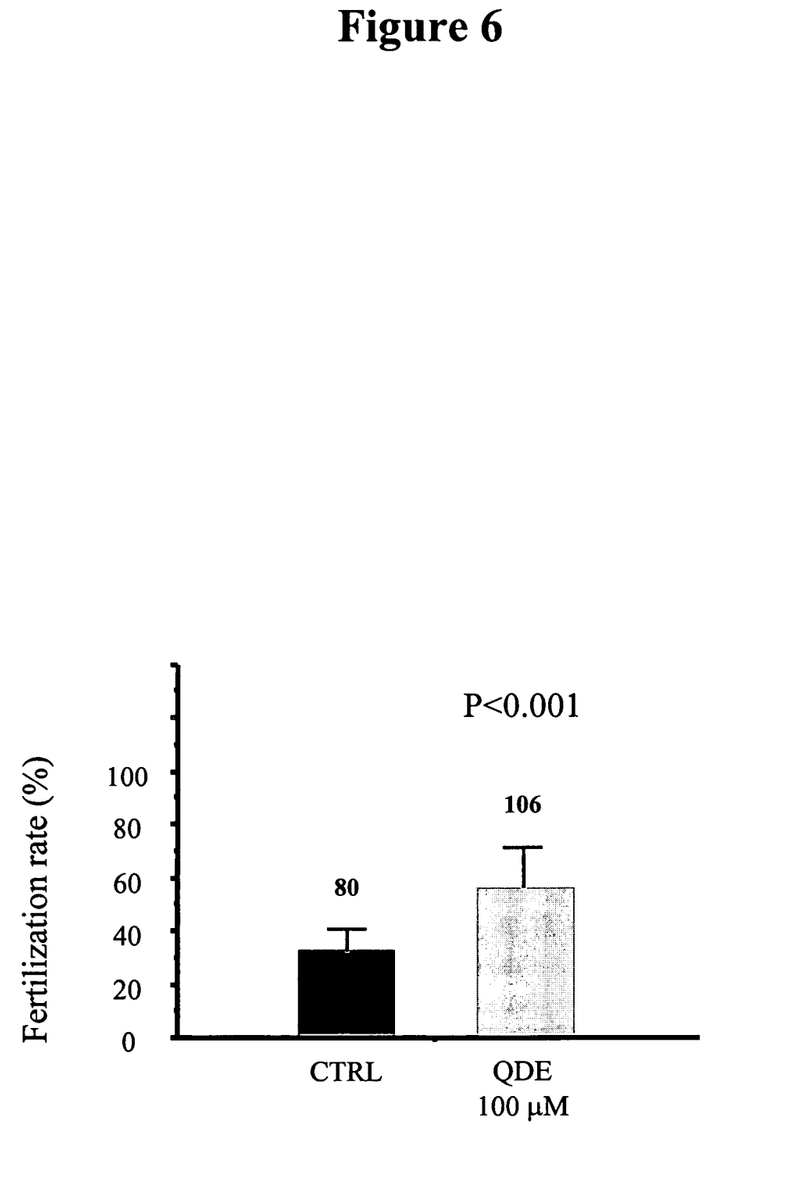
FIG. 6. Effect of ODEc on in vitro fertilization of intact oocytes in mice.

By conventional IVF: The three experiments gave similar results with a mean fertilization rate of 32.1+7.6% for the controls and 56.3+16.0% for the test group (P<0.001) (FIG. 6).

Discussion

The number of spermatozoa that fused with a zona-free oocyte was approximately twenty in humans whereas in mice it generally did not exceed two. This number, which increased to a lesser extent than in humans under the effect of QDE, rapidly reached statistical significance. Furthermore, during in vitro fertilization of intact oocytes, QDEc led to a 75% increase in the normal oocyte fertilization rate. The interaction of the spermatozoon with the oocyte membrane therefore appears to be similar in mice and humans. The cyclized version of the peptide which mimics the disintegrin binding site of fertilin beta clearly increases the fusiogenic capacity of gametes.

LEGENDS OF FIGURES

The zona pellucida was mechanically removed from the oocytes which were then incubated for 45 minutes with 100 µM biotinylated peptide. The FEEc peptide was detected with a mouse anti-biotin antibody recognized by a biotinylated anti-mouse immunoglobulin antibody then by streptavidin-FITC. The oocytes were then mounted in immunomount between the coverslip and the slide and examined under a confocal microscope, B: superimposition of sections corresponding to a hemi-oocyte.

Intact oocytes were incubated with 200 µM FEEc peptide for 45 minutes. They were washed, incubated with 20 µM anti-integrin α6 subunit antibody for 45 minutes, then fixed in 4% PFA for 30 minutes. They were washed, incubated with a second rhodamine-labelled anti-mouse immunoglobulin antibody and examined by immunofluorescence. FIG. 2A: control oocyte showing diffuse, homogeneous fluorescence on the oocyte surface. FIG. 2B: after incubation with FEEc peptide, the α6 subunit redistributed to form membrane patches.

Zona-free oocytes were incubated in 20 μl drops of culture medium under oil with 4000 mobile spermatozoa for 18 hours. They were then washed and incubated in 10 μM Hoechst 33342 for 30 minutes and washed again, mounted in immunomount between the coverslip and the slide and examined under ultraviolet light. FIG. 3A: control oocyte showing the presence of about twenty fused spermatozoa in the oocyte cytoplasm. FIG. 3B: oocyte co-incubated with 100 μM FEEc peptide showing about sixty fused spermatozoa.

Comparison of fertilization rates obtained in the presence and absence of 100 μM FEEc peptide in the incubation medium.

The numbers in parentheses represent the number of oocytes in each group. Statistically different from control group: *($P<0.05$); **($P<0.04$)

REFERENCES

Accession Number: Mouse Q60718; Human Q99965; Guinea pig Q60411; Rabbit Q28660; Macaque Q28478; Bovine O77780; Rat Q63202; Pig CAC84225.

Aytoz A, Van den Abbeel E, Bonduelle M, Camus M, Joris H, Van Steirteghem A, Devroey P. Obstetric outcome of pregnancies after the transfer of cryopreserved and fresh embryos obtained by conventional in-vitro fertilization and intracytoplasmic sperm injection. Hum Reprod. 1999 October; 14(10):2619-24.

Bavister B D. Early history of in vitro fertilization. Reproduction. 2002 August; 124(2):181-96.

Bronson R A, Fusi F M, Calzi F, Doldi N, Ferrari A. Evidence that a functional fertilin-like ADAM plays a role in human sperm-oolemmal interactions. Mol Hum Reprod. 1999 May; 5(5):433-40.

Evans J P. The molecular basis of sperm-oocyte membrane interactions during mammalian fertilization. Hum Reprod Update. 2002 July-August; 8(4):297-311. Review.

Evans J P. Fertilin beta and other ADAMs as integrin ligands: insights into cell adhesion and fertilization. Bioessays. 2001 July; 23(7):628-39. Review.

Evans J P, Schultz R M, and Kopf G S. Mouse sperm-egg plasma membrane interactions: analysis of roles of egg integrins and the mouse sperm homologue of PH-30 (fertilin)β. J Cell Sci. 1995, 108:3267-3278.

Gupta S K, Alves K, Palladino L O, Mark G E, Hollis G F. Molecular cloning of the human fertilin beta subunit. Biochem Biophys Res Commun. 1996 Jul. 16; 224(2):318-26.PMID: 8702389.

Gupta S, Li H, Sampson N S. Characterization of fertilin beta-disintegrin binding specific in sperm-egg adhesion. Bioorg Med Chem 2000 April; 8(4):723-9.

Kowalik A, Palermo G D, Barmat L, Veeck L, Rimarachin J, Rosenwaks Z. Comparison of clinical outcome after cryopreservation of embryos obtained from intracytoplasmic sperm injection and in-vitro fertilization. Hum Reprod. 1998 October; 13(1O):2848-51.

Li H, Sampson N. Structural analysis of fertilin(beta) cyclic peptide mimics that are ligands for alpha6beta1 integrin. J Pept Res 2002 February; 59(2):45-54.

Myles D G, Kimmel L H, Bolbel C P, White J M, and Primakoff P. Identification of a binding site in the disintegrin domain of fertilin required for sperm-egg fusion. Proc Natl Acad Sci USA 1994, 91:4195-4198.

Mwethera P G, Makokha A, Chai D. Fertilin beta peptides inhibit sperm binding to zona-free egg in a homologous baboon in vitro fertilization system. Contraception 1999 February; 59(2): 131-5

Simon A, Holzer H, Hurwitz A, Revel A, Zentner B S, Lossos F, Laufer N. Comparison of cryopreservation outcome following intracytoplasmic sperm injection and conventional in vitro fertilization. J Assist Reprod Genet. 1998 August; 15(7):431-7.

Swann K. Ca(2+) oscillations and sperm factors at fertilization in mammals. Hum Fertil (Camb). 1999; 2(1):61-66.

Swann K, Parrington J, Jones K T. Potential role of a sperm-derived phospholipase C in triggering the egg-activating Ca2+ signal at fertilization. Reproduction. 2001 December; 122(6):839-46. Review.

Tesarik J, Mendoza C, Greco E. Paternal effects acting during the first cell cycle of human preimplantation development after ICSI. Hum Reprod. 2002 January; 17(1):184-9.

Vidaeus C M, von Kapp-Herr C, Golden W L, Eddy R L, Shows T B, Herr J C. Human fertilin beta: identification, characterization, and chromosomal mapping of an ADAM gene family member. Mol Reprod Dev. 1997 March; 46(3): 363-9.

The invention claimed is:

1. A cyclic peptide having the ability to increase the fusiogenic capacity of a gamete and consisting of the following formula:

wherein X represents an amino acid which can be different or identical for each occurrence, and m+n is less than or equal to 5.

2. The cyclic peptide according to claim 1, wherein said peptide consists of the following formula:

(SEQ ID NO: 17)

where X is an amino acid or is selected from the group consisting of A, S or T.

3. The cyclic peptide according to claim 2, wherein X is S.

4. A multimer of cyclic peptides, said peptides having the ability to increase the fusiogenic capacity of a gamete, said cyclic peptides consisting of units of the following formula:

wherein X represents an amino acid which can be different or identical for occurrence, and m+n is less than or equal to 5.

5. The multimer according to claim 4, said peptides consisting of the following formula:

(SEQ ID NO: 17)

wherein X is an amino acid or is selected from the group consisting of A, S or T.

6. A composition intended for gamete culture comprising a peptide according to claim 1 or a multimer according to claim 4.

* * * * *

SEQUENCE LISTING

```
<160> NUMBER OF SEQ ID NOS: 17

<210> SEQ ID NO 1
<211> LENGTH: 30
<212> TYPE: PRT
<213> ORGANISM: Homo sapiens
<220> FEATURE:
<221> NAME/KEY: SITE
<222> LOCATION: (14)..(16)
<223> OTHER INFORMATION: Tripeptide

<400> SEQUENCE: 1

Cys Leu Phe Met Ser Lys Glu Arg Met Cys Arg Pro Ser Phe Glu Glu
1               5                   10                  15
```

Cys Asp Leu Pro Glu Tyr Cys Asn Gly Ser Ser Ala Ser Cys
            20                  25                  30

<210> SEQ ID NO 2
<211> LENGTH: 30
<212> TYPE: PRT
<213> ORGANISM: Mus musculus

<400> SEQUENCE: 2

Cys Lys Leu Lys Arg Lys Gly Glu Val Cys Arg Leu Ala Gln Asp Glu
1               5                   10                  15

Cys Asp Val Thr Glu Tyr Cys Asn Gly Thr Ser Glu Val Cys
            20                  25                  30

<210> SEQ ID NO 3
<211> LENGTH: 30
<212> TYPE: PRT
<213> ORGANISM: Cavia porcellus

<400> SEQUENCE: 3

Cys Glu Phe Lys Thr Lys Gly Glu Val Cys Arg Glu Ser Thr Asp Glu
1               5                   10                  15

Cys Asp Leu Pro Glu Tyr Cys Asn Gly Ser Ser Gly Ala Cys
            20                  25                  30

<210> SEQ ID NO 4
<211> LENGTH: 30
<212> TYPE: PRT
<213> ORGANISM: Oryctolagus cuniculus

<400> SEQUENCE: 4

Cys Thr Phe Lys Glu Arg Gly Gln Ser Cys Arg Pro Pro Val Gly Glu
1               5                   10                  15

Cys Asp Leu Phe Glu Tyr Cys Asn Gly Thr Ser Ala Leu Cys
            20                  25                  30

<210> SEQ ID NO 5
<211> LENGTH: 30
<212> TYPE: PRT
<213> ORGANISM: Macaca fascicularis

<400> SEQUENCE: 5

Cys Leu Phe Met Ser Gln Glu Arg Cys Cys Arg Pro Ser Phe Asp Glu
1               5                   10                  15

Cys Asp Leu Pro Glu Tyr Cys Asn Gly Thr Ser Ala Ser Cys
            20                  25                  30

<210> SEQ ID NO 6
<211> LENGTH: 30
<212> TYPE: PRT
<213> ORGANISM: Bos taurus

<400> SEQUENCE: 6

Cys Ala Phe Ile Pro Lys Gly His Ile Cys Arg Gly Ser Thr Asp Glu
1               5                   10                  15

Cys Asp Leu His Glu Tyr Cys Asn Gly Ser Ser Ala Ala Cys
            20                  25                  30

<210> SEQ ID NO 7
<211> LENGTH: 30
<212> TYPE: PRT
<213> ORGANISM: Rattus norvegicus -continued

```
<400> SEQUENCE: 7

Cys Asn Leu Lys Ala Lys Gly Glu Leu Cys Arg Pro Ala Asn Gln Glu
1               5                   10                  15

Cys Asp Val Thr Glu Tyr Cys Asn Gly Thr Ser Glu Val Cys
            20                  25                  30

<210> SEQ ID NO 8
<211> LENGTH: 30
<212> TYPE: PRT
<213> ORGANISM: Sus scrofa

<400> SEQUENCE: 8

Cys Ser Phe Met Ala Lys Gly Gln Thr Cys Arg Leu Thr Leu Asp Glu
1               5                   10                  15

Cys Asp Leu Leu Glu Tyr Cys Asn Gly Ser Ser Ala Ala Cys
            20                  25                  30

<210> SEQ ID NO 9
<211> LENGTH: 6
<212> TYPE: PRT
<213> ORGANISM: artificial sequence
<220> FEATURE:
<223> OTHER INFORMATION: peptide FEEc
<220> FEATURE:
<221> NAME/KEY: DISULFID
<222> LOCATION: (1)..(6)

<400> SEQUENCE: 9

Cys Ser Phe Glu Glu Cys
1               5

<210> SEQ ID NO 10
<211> LENGTH: 17
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: F or L
<220> FEATURE:
<221> NAME/KEY: MISC_FEATURE
<222> LOCATION: (4)..(4)
<223> OTHER INFORMATION: K, M or I
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: K, R or Q
<220> FEATURE:
<221> NAME/KEY: MISC_FEATURE
<222> LOCATION: (7)..(7)
<223> OTHER INFORMATION: G or E
<220> FEATURE:
<221> NAME/KEY: MISC_FEATURE
<222> LOCATION: (8)..(9)
<223> OTHER INFORMATION: any amino acid
<220> FEATURE:
<221> NAME/KEY: MISC_FEATURE
<222> LOCATION: (12)..(14)
<223> OTHER INFORMATION: any amino acid
<220> FEATURE:
<221> NAME/KEY: MISC_FEATURE
```

```
<222> LOCATION: (15)..(15)
<223> OTHER INFORMATION: Q, D or E

<400> SEQUENCE: 10

Cys Xaa Xaa Xaa Xaa Xaa Xaa Xaa Xaa Cys Arg Xaa Xaa Xaa Xaa Glu
1               5                   10                  15

Cys

<210> SEQ ID NO 11
<211> LENGTH: 23
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: F or L
<220> FEATURE:
<221> NAME/KEY: MISC_FEATURE
<222> LOCATION: (4)..(4)
<223> OTHER INFORMATION: K, M or I
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: K, R or Q
<220> FEATURE:
<221> NAME/KEY: MISC_FEATURE
<222> LOCATION: (7)..(7)
<223> OTHER INFORMATION: G or E
<220> FEATURE:
<221> NAME/KEY: MISC_FEATURE
<222> LOCATION: (8)..(9)
<223> OTHER INFORMATION: any amino acid
<220> FEATURE:
<221> NAME/KEY: MISC_FEATURE
<222> LOCATION: (12)..(14)
<223> OTHER INFORMATION: any amino acid
<220> FEATURE:
<221> NAME/KEY: MISC_FEATURE
<222> LOCATION: (15)..(15)
<223> OTHER INFORMATION: Q, D or E
<220> FEATURE:
<221> NAME/KEY: MISC_FEATURE
<222> LOCATION: (19)..(19)
<223> OTHER INFORMATION: L or V
<220> FEATURE:
<221> NAME/KEY: MISC_FEATURE
<222> LOCATION: (20)..(20)
<223> OTHER INFORMATION: any amino acid

<400> SEQUENCE: 11

Cys Xaa Xaa Xaa Xaa Xaa Xaa Xaa Xaa Cys Arg Xaa Xaa Xaa Xaa Glu
1               5                   10                  15

Cys Asp Xaa Xaa Glu Tyr Cys
            20

<210> SEQ ID NO 12
<211> LENGTH: 30
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
```

```
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: F or L
<220> FEATURE:
<221> NAME/KEY: MISC_FEATURE
<222> LOCATION: (4)..(4)
<223> OTHER INFORMATION: K, M or I
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: K, R or Q
<220> FEATURE:
<221> NAME/KEY: MISC_FEATURE
<222> LOCATION: (7)..(7)
<223> OTHER INFORMATION: G or E
<220> FEATURE:
<221> NAME/KEY: MISC_FEATURE
<222> LOCATION: (8)..(9)
<223> OTHER INFORMATION: any amino acid
<220> FEATURE:
<221> NAME/KEY: MISC_FEATURE
<222> LOCATION: (12)..(14)
<223> OTHER INFORMATION: any amino acid
<220> FEATURE:
<221> NAME/KEY: MISC_FEATURE
<222> LOCATION: (15)..(15)
<223> OTHER INFORMATION: Q, D or E
<220> FEATURE:
<221> NAME/KEY: MISC_FEATURE
<222> LOCATION: (19)..(19)
<223> OTHER INFORMATION: L or V
<220> FEATURE:
<221> NAME/KEY: MISC_FEATURE
<222> LOCATION: (20)..(20)
<223> OTHER INFORMATION: any amino acid
<220> FEATURE:
<221> NAME/KEY: MISC_FEATURE
<222> LOCATION: (25)..(25)
<223> OTHER INFORMATION: G or E
<220> FEATURE:
<221> NAME/KEY: MISC_FEATURE
<222> LOCATION: (26)..(26)
<223> OTHER INFORMATION: T or S
<220> FEATURE:
<221> NAME/KEY: MISC_FEATURE
<222> LOCATION: (28)..(28)
<223> OTHER INFORMATION: A, E or G
<220> FEATURE:
<221> NAME/KEY: MISC_FEATURE
<222> LOCATION: (29)..(29)
<223> OTHER INFORMATION: any amino acid

<400> SEQUENCE: 12

Cys Xaa Xaa Xaa Xaa Xaa Xaa Xaa Cys Arg Xaa Xaa Xaa Xaa Glu
1               5                   10                  15

Cys Asp Xaa Xaa Glu Tyr Cys Asn Xaa Xaa Ser Xaa Xaa Cys
            20                  25                  30

<210> SEQ ID NO 13
<211> LENGTH: 8
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (3)..(5)
<223> OTHER INFORMATION: any amino acid
<220> FEATURE:
```

```
<221> NAME/KEY: MISC_FEATURE
<222> LOCATION: (6)..(6)
<223> OTHER INFORMATION: Q, D or E

<400> SEQUENCE: 13

Cys Arg Xaa Xaa Xaa Xaa Glu Cys
1               5

<210> SEQ ID NO 14
<211> LENGTH: 14
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (3)..(5)
<223> OTHER INFORMATION: any amino acid
<220> FEATURE:
<221> NAME/KEY: MISC_FEATURE
<222> LOCATION: (6)..(6)
<223> OTHER INFORMATION: Q, D or E
<220> FEATURE:
<221> NAME/KEY: MISC_FEATURE
<222> LOCATION: (10)..(10)
<223> OTHER INFORMATION: L or V
<220> FEATURE:
<221> NAME/KEY: MISC_FEATURE
<222> LOCATION: (11)..(11)
<223> OTHER INFORMATION: any amino acid

<400> SEQUENCE: 14

Cys Arg Xaa Xaa Xaa Xaa Glu Cys Asp Xaa Xaa Glu Tyr Cys
1               5                   10

<210> SEQ ID NO 15
<211> LENGTH: 21
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (3)..(5)
<223> OTHER INFORMATION: any amino acid
<220> FEATURE:
<221> NAME/KEY: MISC_FEATURE
<222> LOCATION: (6)..(6)
<223> OTHER INFORMATION: Q, D or E
<220> FEATURE:
<221> NAME/KEY: MISC_FEATURE
<222> LOCATION: (10)..(10)
<223> OTHER INFORMATION: L or V
<220> FEATURE:
<221> NAME/KEY: MISC_FEATURE
<222> LOCATION: (11)..(11)
<223> OTHER INFORMATION: any amino acid
<220> FEATURE:
<221> NAME/KEY: MISC_FEATURE
<222> LOCATION: (16)..(16)
<223> OTHER INFORMATION: G or E
<220> FEATURE:
<221> NAME/KEY: MISC_FEATURE
<222> LOCATION: (17)..(17)
<223> OTHER INFORMATION: T or S
<220> FEATURE:
<221> NAME/KEY: MISC_FEATURE
<222> LOCATION: (19)..(19)
<223> OTHER INFORMATION: A, E or G
<220> FEATURE:
<221> NAME/KEY: MISC_FEATURE
<222> LOCATION: (20)..(20)
<223> OTHER INFORMATION: any amino acid

<400> SEQUENCE: 15
```

-continued

```
Cys Arg Xaa Xaa Xaa Xaa Glu Cys Asp Xaa Xaa Glu Tyr Cys Asn Xaa
1 5 10 15

Xaa Ser Xaa Xaa Cys
20

<210> SEQ ID NO 16
<211> LENGTH: 6
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (2)..(3)
<223> OTHER INFORMATION: any amino acid
<220> FEATURE:
<221> NAME/KEY: MISC_FEATURE
<222> LOCATION: (4)..(4)
<223> OTHER INFORMATION: Q, D or E

<400> SEQUENCE: 16

Cys Xaa Xaa Xaa Glu Cys
1 5

<210> SEQ ID NO 17
<211> LENGTH: 6
<212> TYPE: PRT
<213> ORGANISM: artificial sequence
<220> FEATURE:
<223> OTHER INFORMATION: cyclic peptide
<220> FEATURE:
<221> NAME/KEY: MISC_FEATURE
<222> LOCATION: (2)..(2)
<223> OTHER INFORMATION: any amino acid

<400> SEQUENCE: 17

Cys Xaa Phe Glu Glu Cys
1 5
```